United States Patent [19]

Watkins

[11] 4,227,806
[45] Oct. 14, 1980

[54] METHODS FOR NON-DESTRUCTIVELY DETERMINING PARAMETERS OF AN OPTICAL FIBER PREFORM

[75] Inventor: Laurence S. Watkins, Hopewell Township, Mercer County, N.J.

[73] Assignee: Western Electric Company, Inc., New York, N.Y.

[21] Appl. No.: 951,807

[22] Filed: Oct. 16, 1978

[51] Int. Cl.³ ............................................. G01N 21/47
[52] U.S. Cl. .................................................. 356/73.1
[58] Field of Search ........................................ 356/73.1

[56] References Cited

U.S. PATENT DOCUMENTS

| | | | |
|---|---|---|---|
| 3,636,360 | 1/1972 | Oishi et al. | 250/218 |
| 3,765,774 | 10/1973 | Petrohilos | 356/387 |
| 3,873,208 | 3/1975 | Southwell | 356/128 |
| 3,879,128 | 4/1975 | Presby | 356/73 |
| 4,021,217 | 5/1977 | Bondybey et al. | 356/239 X |
| 4,027,977 | 6/1977 | Frazee, Jr. et al. | 250/550 X |

OTHER PUBLICATIONS

"Automatic Analysis of Interferograms: Optical Waveguide Refractive Index Profiles" by Wonsiewicz et al., *Applied Optics*, vol. 15, No. 4, Apr. 1976.
"Refractive-Index Profile of an Optical Fiber: Its Measurement by the Scattering-Pattern Method" by Okoshi et al., *Applied Optics*, vol. 15, No. 11, Nov. 1976.
"Refractive Index Profiling of Graded Index Optical Fibers" by Presby et al., *Rev. Sci. Instrum.*, vol. 47, No. 3, Mar. 1976.
"Low-Loss Optical Waveguides with Pure Fused SiO₂ Cores" by Tasker et al., *Proceedings of the IEEE*, Sep. 1974.
"A New Technique for the Preparation of Low-Loss and Graded-Index Optical Fibers" by MacChesney et al., *Proceedings of the IEEE*, Sep. 1974.
"Refractive-Index Profile Determination of Optical Fibers from the Diffraction Pattern" by E. Brinkmeyer, *Applied Optics*, vol. 16, No. 11, Nov. 1977.
"Refractive-index Profile Determination of Optical Fibers by Spatial Filtering" by E. Brinkmeyer, *Applied Optics*, vol. 17, No. 1, Jan. 1978.
"Nondestructive Measurement of Index Profile of an Optical-Fibre Preform" by P. L. Chu, *Electronics Letters*, vol. 13, No. 24, Nov. 24, 1977.
"Scattering from Side-Illuminated Clad Glass Fibers for Determination of Fiber Parameters" by L. S. Watkins, *Journal of the Optical Society of America*, vol. 64, No. 6, Jun. 1974.

*Primary Examiner*—Vincent P. McGraw
*Attorney, Agent, or Firm*—D. J. Kirk

[57] ABSTRACT

A narrow laser beam (16) scans a clad optical fiber preform (10) with a narrow, parallel scanning beam of coherent light and the deflection angle ($\theta$) thereof measured as the beam exits the preform. The deflection angles ($\theta$) of the scanning beam (16) are measured and compared to theoretical or empirically developed deflection angle scans of preforms having known parameters to determine the parameters of the preform. The deflection angle ($\theta$) is plotted versus the incident beam position (d) and that plot is integrated to provide a curve (47) that is compared to theoretically developed plots having known parameters to determine parameters of the fiber preform such as refractive index gradient power, $\gamma$, and the refractive index ratio, $\Delta$.

12 Claims, 15 Drawing Figures

METHODS FOR NON-DESTRUCTIVELY DETERMINING PARAMETERS OF AN OPTICAL FIBER PREFORM

TECHNICAL FIELD

The invention is directed to a method for determining various parameters of an optical fiber preform. In particular, the invention is directed to a non-destructive technique which determines various parameters of such preforms from measurements of the deflection of a scanned beam of light passing through the preform.

BACKGROUND OF THE INVENTION

Presently, there are two principle techniques used for commercial fabrication of optical fiber preforms—the "soot deposition" process and the modified chemical vapor deposition (MCVD) process. These processes involve the thermochemical production of glass from appropriate glass precursor vapor.

In the soot deposition process, the glass precursor vapor is introduced into a hydrolyzing flame and particulate material, commonly referred to as soot, is formed. The stream of particulate material emanating from the flame is directed toward a mandril, which may be, for example, a cylindrical tube or a glass rod, on which the soot is deposited. Following such deposition, the soot is consolidated into a transparent glass, the mandril removed and the resultant hollow tube collapsed to form a solid, cylindrical optical fiber preform.

In the MCVD process, which is summarized in an article titled "Reproducibility of Optical Fibers Prepared by a Modified Chemical Vapor Deposition Process" by F. V. DiMarcello et al. in the *Bell System Technical Journal*, Vol. 57, No. 6, July—August 1978, page 1723 et seq. a stream of glass precursor vapor is directed through the center of a glass tube. The tube is usually composed of glass material which may be appropriate for use as a cladding in the fiber. The tube is heated, causing the gas vapor to react with the inner wall of the tube to cause a glass layer to deposit thereon. The absence of a flame in direct contact with the gas results in a preform having high glass purity and low optical losses. When a sufficient number of such glass layers have been deposited on the inner wall of the tube, the resulting cylinder will also be collapsed to form the solid preform having a substantially cylindrical core encased within a surrounding cladding.

In both methods, a number of sequential passes are made to deposit a plurality of concentric layers of material to obtain the desired thickness. All layers may have the same refractive index resulting in a step index preform, or each layer may have a slightly different refractive index resulting in a graded index preform. The graded index preform will have an increasing refractive index towards the center of the preform resulting in a substantially parabolic refractive index profile.

The refractive index profile of an optical fiber preform is expressed, by those knowledgeable in the art, in the form of $$n(r) = n_0 \left[ \frac{1 - 2\Delta \left( \frac{r}{a} \right)^\gamma}{1 - 2\Delta} \right]^{\frac{1}{2}}$$

where:
 $n$ = refractive index
 $r$ = radius position in preform
 $a$ = radius of the core
 $n_0$ = at $r = a$, at the edge of the core region, typically the cladding refractive index
 $\gamma$ = refractive index gradient power
 $\Delta$ = refractive index ratio.

Those skilled in the art use the refractive index gradient power $\gamma$ and the refractive index ratio $\Delta$ to determine the character and acceptability of the profile, $n(r)$, of the graded index preform. Variations in the parameter $\gamma$ result in a change in the shape of the desired parabolic profile while changes in the parameter $\Delta$ will cause proportionate changes in the height of the profile.

The refractive index profile of an optical fiber is substantially the same as the profile of the preform from which it was drawn. Therefore, deviations from the parabolic refractive index profile $n(r)$ of the preform may result in unacceptable transmission characteristics of the fiber drawn therefrom. Thus, it becomes most advantageous to determine the parameters $\gamma$ and $\Delta$ to characterize the refractive index profile of the preform prior to drawing fiber therefrom to avoid the expense of producing kilometers of optical fiber that would be unacceptable for its intended use.

One method for determining $\gamma$ and $\Delta$ of a drawn fiber is described in an article titled "Automatic Analysis of Interferograms: Optical Waveguide Refractive Index Profiles" by B. C. Wonsiewicz et al. in *Applied Optics*, Vol. 15, No. 4, April 1976, page 1048 et seq. That article describes a method which provides a computer-generated plot of the refractive index profile $n(r)$ versus the radius of an optical fiber. The data are obtained from the pattern of a thin, polished cross section of a fiber as viewed in an interference microscope. The interference pattern is digitized with a scanning microdensitometer, followed by a computer determination of the position of the center line of each interference fringe. A computer program determines the value of $\gamma$ corresponding to the curve that best fits the data in the aforementioned equation for the profile $n(r)$. The value for $\Delta$ is determined from the maximum of the profile $n(r)$ of the plot. Although such a method can effectively determine the profile of the optical fiber, it is destructive, time consuming and expensive.

Nondestructive methods using diffraction techniques such as described in an article titled "Refractive-index profile determination of optical fibers, from the diffraction pattern" by Ernst Brinkmeyer, in *Applied Optics*, Vol. 16, No. 11, November 1977, pages 2802 and 2803, have been used to obtain the refractive index profile of an optical fiber. However, as previously indicated, determining the parameters after the fiber is drawn can be wasteful of time and material.

Thus, there is a need for a non-destructive, non-contact method of determining the refractive index profile parameters of an optical fiber preform.

SUMMARY OF THE INVENTION

The instant invention solves the foregoing problem with a method of determining parameters of a cylindrical optical fiber preform having a core and a cladding, comprising the steps of: scanning at least a portion of the cylindrical surface of the preform with a narrow, parallel scanning beam of coherent light, the parallel scanning beam being located within a plane which is perpendicular to the longitudinal axis of the preform, said beam passing through and being refracted by said preform; detecting the angular deflections of the refracted scanning beam exiting the preform; and comparing the detected angular deflections of the scanning beam with angular deflections of beams passing through preforms having known parameters to determine the parameters of the preform.

DETAILED DESCRIPTION

The instant invention is set forth in the context of non-destructively determining parameters of a graded index optical fiber preform. However, such description is for purposes of exposition and not for limitation and preforms having other profiles (e.g., step index) could be characterized using the instant techniques.

Figure 1:
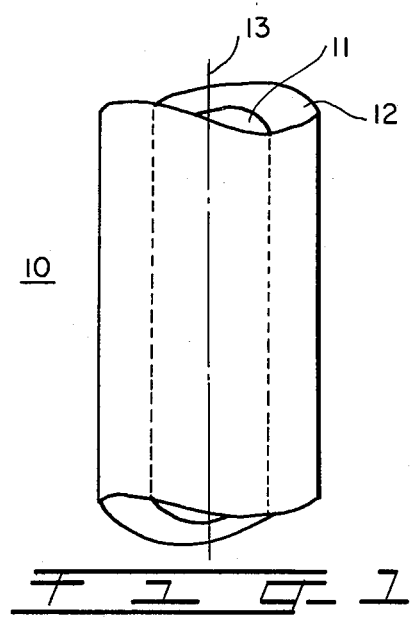
FIG. 1 is a partial sectional view of an optical fiber preform.

FIG. 1 depicts a section of an optical fiber preform, generally designated by the numeral 10, which is comprised of a substantially cylindrical core 11 surrounded by a cladding 12 which may have been fabricated by any of the well known prior art techniques. The core 11 has a slightly higher refractive index than the cladding 12. In the graded index preform 10 of the exemplary embodiment, the refractive index of the core 11 increases towards the axis 13 of the preform resulting in a substantially parabolic refractive index profile n(r).

Figure 2:
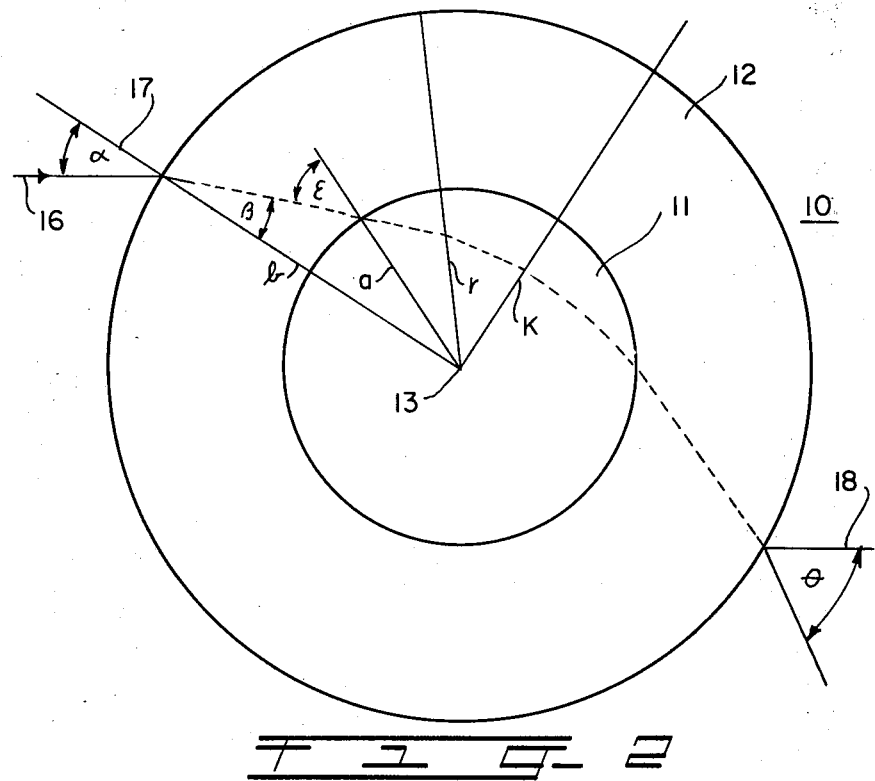
FIG. 2 is an enlarged cross-sectional view of the preform shown in FIG. 1.

FIG. 2 is an enlarged cross-section of the preform 10, shown in FIG. 1, taken in a plane perpendicular to the axis 13 of the preform. A narrow light beam 16 is shown directed toward the preform 10 perpendicular to an imaginary plane that contains the preform axis 13. A trace of the beam 16 being refracted by the preform 10 is shown as dashed lines. As can be seen, the amount that the beam 16 is deflected or refracted is a function of the refractive index properties of the core 11. The angle $\alpha$ is the incident angle between the beam 16 and a radial line 17 drawn from the axis 13 and extending through the point at which the ray 16 contacts the preform 10. The angle $\theta$ is the deflection angle between a line 18, which is parallel to the incident beam 16, and the refracted beam 16 as it exits the preform 10.

When the incidence angle $\alpha$ is sufficiently large, greater than $\alpha_c$, the beam 16 only traverses the cladding 12. There is a deflection angle $\theta_c$ which can be associated with this and occurs when the ray 16 just misses the core 11. $\theta_c$ and $\alpha_c$ are defined as follows:

$$\alpha_c = \sin^{-1}\left(\frac{a\,n_c}{b\,n_a}\right) \tag{1}$$

$$\theta_c = 2\left[\sin^{-1}\left(\frac{a\,n_c}{b\,n_a}\right) - \sin^{-1}\left(\frac{a}{b}\right)\right] \tag{2}$$

where a is the radius of the core 11, b is the radius of the preform 10, $n_c$ is the refractive index of the cladding 12 and $n_a$ is the refractive index of the surrounding media (e.g., oil, air).

Figure 3:
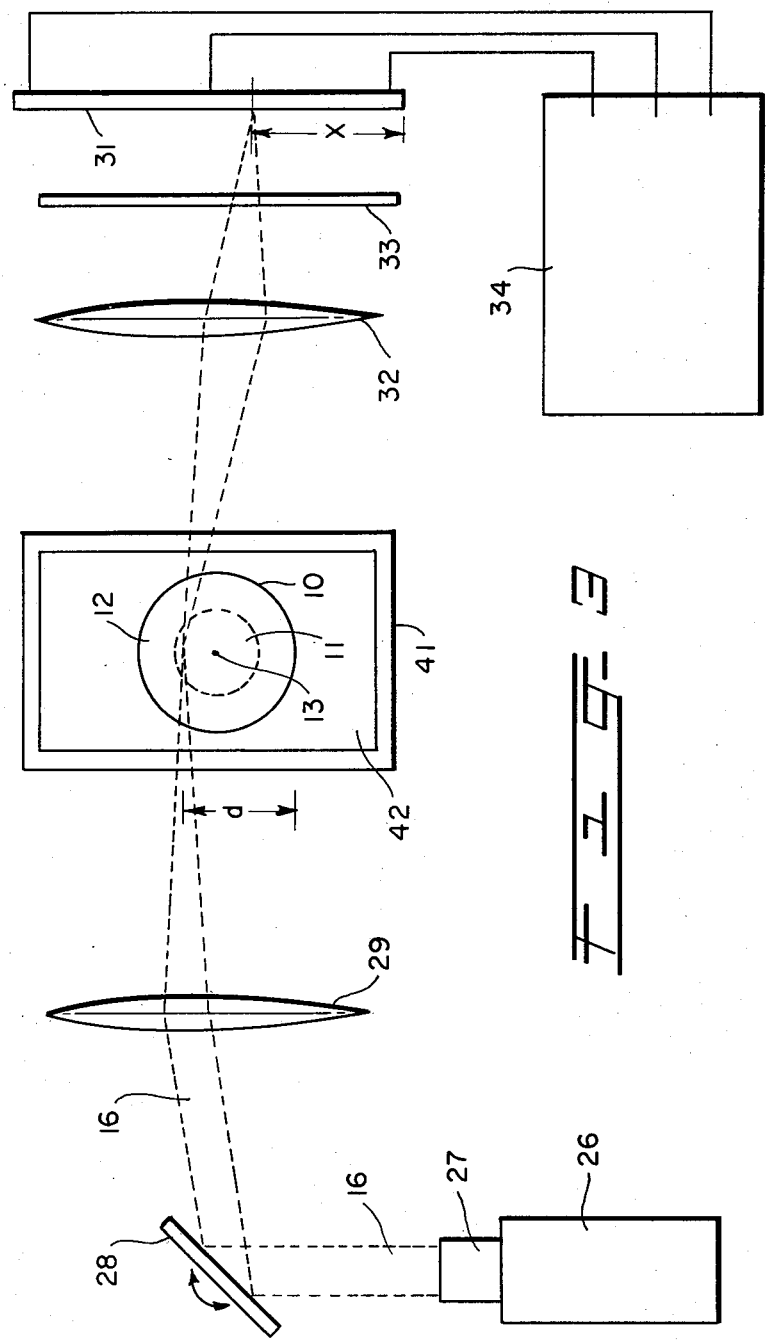
FIG. 3 is a diagrammatic representation of an exemplary embodiment of the apparatus of the instant invention.

FIG. 3 is a plan view of a preferred embodiment of the instant invention. A laser 26 (e.g., HeNe), or other coherent light source, generates a beam 16 which passes through a beam expander 27 and is reflected from a rotatable galvanometer controlled mirror 28 and then focussed onto the preform 10 by a telecentric lens 29. The beam 16, having a circular cross section with a diameter in the range of 20 to 30 microns in the preform 10, is refracted by the preform and focused onto a linear position sensor 31 via a second lens 32 and a cylindrical lens 33. The position sensor 31 has output terminals A and B connected to a monitoring apparatus 34.

The preform 10 may be placed in a glass tank 41 containing an index matching oil 42 having a refractive index substantially the same as that of the cladding 12. The purpose of the index matching oil 42 is to substantially eliminate unpredictable variations in the refraction of the beam 16 at the outer surface of the preform 10 due to non-circularity of that surface. However, the use of the oil 42 may not be necessary when accuracy is not critical or if the preform 10 under test has a cross section that is circular to a high degree of accuracy.

In order to be able to determine the position (d) of the beam 16, the mirror 28 is rotated to make the beam 16 just graze the surface on opposite sides of the preform 10 and the respective mirror angles are recorded. This determines the position of the preform 10 and subsequent readings of the angular position of the mirror 28 can be used to determine any intermediate position d. The mid-point of the two grazing incidence measurements is assumed to be the center of the preform 10 for the purposes of calculating the distance d.

The lateral position x of the beam 16 in the focal plane (i.e., the plane of the linear position sensor 31) is a function of the deflection angle, $\theta$, (see FIG. 2) of the beam which is given by $$\theta = \tan^{-1}(x/f) \tag{3}$$

where f is the focal length of the lens 32.

The linear position sensor 31 as well as the monitoring apparatus 34 may be any of those well known in the art which can determine the location of a beam of light impinging thereon and provide an electrical output indicative of that location. A particular apparatus used in a working embodiment was a silicon photodiode sensor and preamplifier manufactured by United Detector Technology, Inc., Santa Monica, Calif.

In operation, the incident beam 16 is scanned along a portion of the outer surface of the preform 10 using a slow scanning galvanometer to drive the mirror 28. The galvanometer is driven by a ramp generator, in a well-known manner, to give a constant velocity sweep. Although the beam 16 is reflected onto the lens 29 at different angles as the mirror 28 rotates, the lens is so constructed that the beam will always leave the lens in the same direction as shown in U.S. Pat. No. 3,765,774 which issued on Oct. 16, 1973 to Petrohilos. Accordingly, a portion of the cylindrical surface of the preform 10 is scanned with a narrow, parallel scanning beam of coherent light. The parallel scanning beam 16 is located within a plane that is normal to the longitudinal axis 13 of the preform 10 and optimally is also perpendicular to a plane containing the longitudinal axis 13 of the preform. The parallel scanning beam 16 will be refracted by the preform 10 and the refracted beam will be directed onto the position sensor 31 via lenses 32 and 33.

The electrical output at the A and B terminals of the sensor 31 are analyzed using the monitoring apparatus 34 to provide a voltage proportional to the deflection angle $\theta$ (see FIG. 2). The approximation $\theta \approx \tan\theta$ is used for equation (3). The maximum angle to be measured is about 10° so that less than 1% error is incurred.

Figure 4:
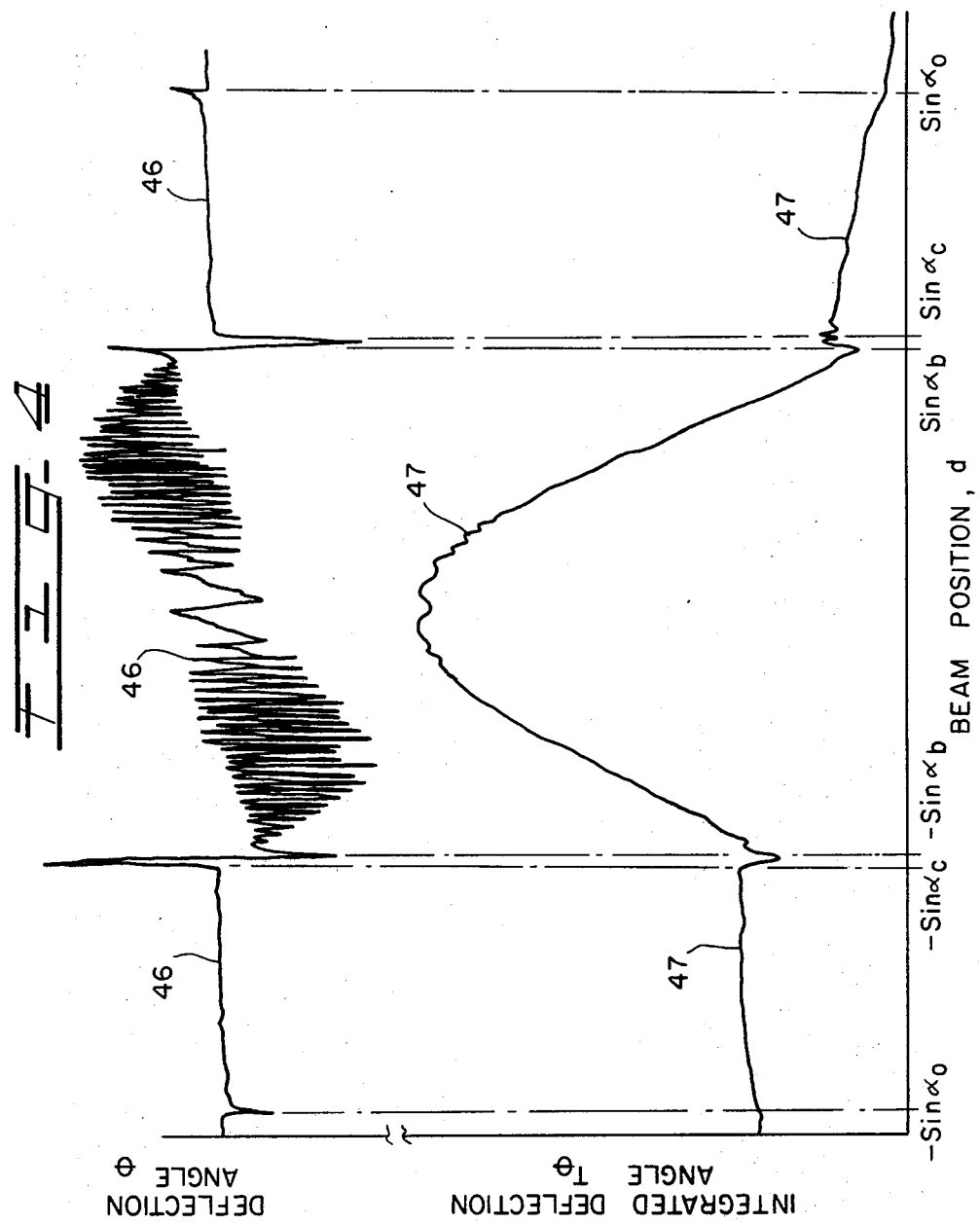
FIG. 4 is a plot of the deflection angle and the integrated deflection angle versus beam position in the preform.

The galvanometer deflection voltage and the measured deflection angle voltage are applied to an X-Y recorder (not shown) to give an experimental plot of deflected angle $\theta$ against the beam position, d, as shown in the upper portion of FIG. 4.

The vertical axis shown in the upper portion of FIG. 4 is the deflection angle $\theta$. The horizontal axis is the position, d, of the incident scanning beam 16 as indicated by the galvanometer voltage controlling the movement of mirror 28 and is equivalent to the radial position of the beam in the preform 10 in the axial plane perpendicular to the direction of the beam.

If the scan 46 in FIG. 4 is observed from left to right, the following observations can be made. Initially, the deflection angle $\theta = 0$ since the beam 16 is in the index matching oil 42 only. The refractive index of the oil 42 is slightly lower than that of the cladding 11 so that when the beam 16 strikes the edge of the preform 10 there is a small negative deflection of the beam. (This is useful in allowing determination of the outer dimensions of the preform 10). As the beam 16 is moved toward the center of the preform 10, the deflection angle $\theta$ moves towards zero as the incidence angle $\alpha$ becomes smaller.

When the beam 16 starts to be refracted by a thin barrier region (not shown) between the core 11 and the cladding 12, the deflection is positive due to the lower refractive index relative to the cladding. As the beam 16 is moved closer to the center of the preform 10, it starts to be refracted into the core 11 which has a higher refractive index; as a consequence the beam is now deflected negatively. With further movement of the beam 16, the mean value of the deflection angle $\theta$ stays negative until the center of the preform 10 is reached. However, there is a large variation of the deflection angles $\theta$ which is a manifestation of the inhomogeneity of the concentric layers which form the core 11. Index gradients in the layers themselves, cause local deflection of the beam 16 which becomes superimposed onto the accumulated deflection due to the overall index gradient. This effect is paramount at the point where the beam 16 is tangential to the layer because it propagates furthest in that layer.

At the center of the preform 10 the deflection angle $\theta$ is zero and then the effect repeats itself (inverted) as the beam 16 traverses the other half of the preform 10.

The plot 46 allows accurate determinations of the geometric dimensions of the preform 10 by measuring the distance, d, for quantities $\sin \alpha_o$ and $\sin \alpha_c$; this provides core diameter, outer diameter and core-cladding concentricity results. In addition, the oscillatory variation of the deflection angle $\theta$ (plot 46) allows a qualitative picture of the uniformity and homogeneity of the deposited layers. Finally, comparison with the theoretical data provides determination of the barrier layer refractive index and thickness.

While the plot 46 presents a usable representation of the deflection angles $\theta$ versus the position, d, of the beam 16 the problem of the layer inhomogeneity remains. When the preform 10 has a core 11 comprised of reasonably homogeneous layers, the aforementioned comparison will provide accurate results. However, there will be inaccuracies in comparing empirical or theoretically developed curves to this data in an attempt to determine the refractive index ratio $\Delta$ and the refractive index gradient power $\gamma$ of the preform 10 when severe inhomogeneities exist in the layers.

In order to provide usable data in such a case, the plot 46 of the deflection angle $\theta$ was integrated resulting in the curve 47 of the integrated deflection angle, $T_\theta$, shown in the lower portion of FIG. 4 where the integrated deflection angle $T_\theta$ is given by:

$$T_\theta = \int_{d=-a}^{d=a} \theta \, dd \qquad (4)$$

where d is the normalized radial distance (the edge of the preform = 1.0) and is equivalent to $d = \sin\alpha$. The curve 47 is realized by sending the measured deflection voltage from the monitoring apparatus 34 to an analogue integrating circuit (not shown). Since this integrates with respect to time, it is important that the galvanometer controlling the movement of the mirror 28 to scan the beam 16 across the preform 10 via lens 29 does so at constant velocity so that the integrated signal is an accurate representation of the deflected signal.

As can be seen, the curve 47 is much smoother and more suitable than the plot 46 for comparison with theoretical or empirically developed curves. The curve 47 is not symmetrical due to a combination of two factors; very small drifts in the signal amplifiers cause a bias into the integrator, and non-symmetry of the core 11 means that the integrated signal will not return to zero at the edge of the core.

The integrated deflection angle curve 47 can now be compared to similar curves resulting from scanned preforms 10 having known values of $\gamma$ and $\Delta$. Although such a method requires storage of a substantial amount of empirical data, the desired parameters can be determined to a high degree of accuracy. Such comparisons can be accomplished by displaying the curves on a cathode ray tube, comparing equations of the curves in a computer or other well-known comparing means.

Figure 5:
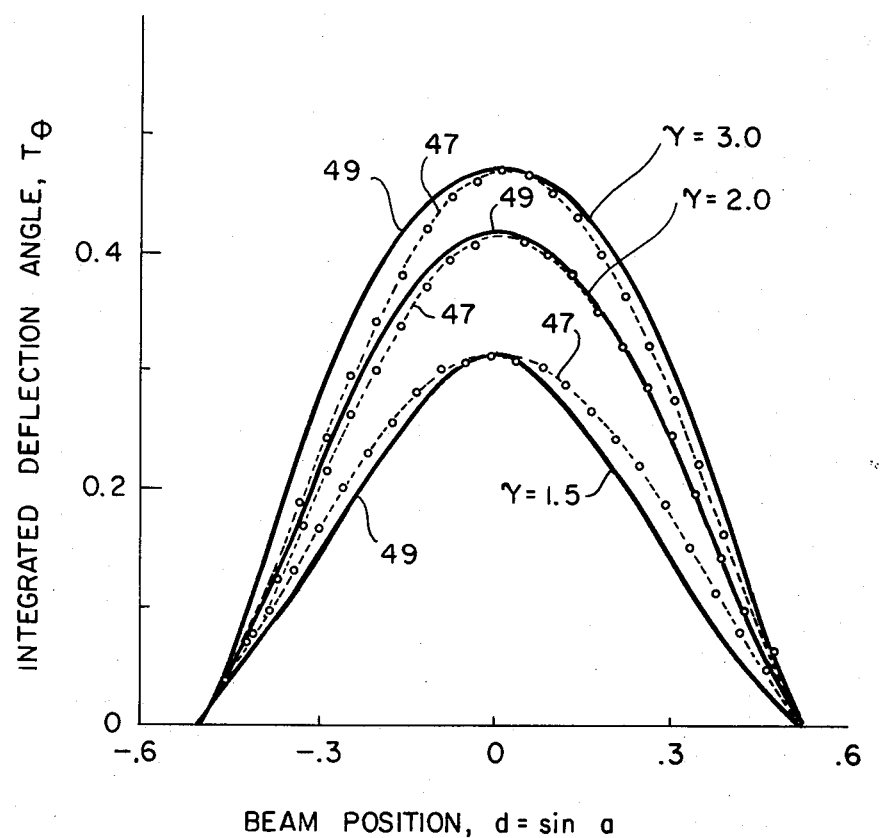
FIG. 5 depicts curves of integrated deflection angles compared with theoretical curves.

Another technique which can be used is to compare the experimental integrated deflection angle curves 47 to theoretically developed deflection angle curves. Such theoretical deflection angle curves 49—49 are shown in FIG. 5 and can be calculated by using the following equation developed by E. W. Marchand and described in an article titled "Ray Tracing in Gradient-Index Media" in the *Journal of the Optical Society of America*, 60, 1, (1970):

$$\theta = 2\left[(\alpha - \beta) + K \int_a^K \frac{dr}{r\sqrt{n(r)^2 r^2 - K^2}}\right]$$

where K is the closest distance between the deflected beam 16 in the preform 10 and the axis 13, as shown in FIG. 2, K may be determined by the following equations which are set out on page 123 of M. Born and E. Wolf "Principles of Optics," 3d ed. (1964):

| | | |
|---|---|---|
| $Kn(K)$ | $= n_c a \sin \xi$ | (6) |
| | $= n_c b \sin \beta$ | (7) |
| | $= n_a b \sin \alpha$ | (8) | where:
 $\xi$ is the incidence angle of the beam on the core/cladding interface; and
 $\beta$ is the angle of refraction of the beam in the cladding.

In order to compare the data with theoretical deflection angle curves 49-49, the curve 47, in FIG. 4, must be adjusted to level it with respect to the horizontal axis. This is done by constructing a pseudohorizontal axis which connects the two sides of the curve 47 in FIG. 4 at the edges of the core region ($\sin \alpha_b$). The integrated deflection angle, $T_\theta$, points on the curve 47 are then referenced to this line as zero and are compared with curves 49—49. Only the core region 11, excluding any barrier layer, is compared. This procedure also removes the small offset generated in the cladding 12 which is the result of integrating the small negative deflection angle signal near the outer edge of the preform 10 produced by the slight mismatch in refractive indices of the cladding 11 and the matching oil 42.

FIG. 5 shows theoretically calculated curves 49—49 of the integrated deflected angle $T_\theta$ for three values of refractive index gradient power, $\gamma = 1.5$, 2.0 and 3.0; the refractive index ratio, $\Delta = 0.01$ and the core-to-cladding diameter ratio was 52.6%. The refractive index of the cladding 12 was 1.457 and the barrier layer had a refractive index of 1.454 with a thickness equal to 5.6% of the radius of the core 11.

As can be seen in FIG. 5, the variation in index gradient power $\gamma$ causes a change in the shape of the theoretical curve 49. If the curves 49—49 were plotted for a fixed value of refractive index gradient power $\gamma$, varying the refractive index ratio $\Delta$ for each curve would cause the height of the curves to increase with increasing $\Delta$, however, the shape would stay the same.

The experimental curves 47—47 are definitely smooth enough to use curve fitting techniques to obtain a reasonable match with the theoretical curves 49—49 and there is a sufficient sensitivity with the refractive index gradient power $\gamma$ to allow $\gamma$ to be determined with reasonable accuracy.

The theoretical curves 49 representing the core 11 are first normalized in both x and y axes to unity values and then fitted to a polynomial fourth order equation using well-known curve fitting techniques. The polynomial is of the form:

$$t_\theta = B_o + B_2 s^2 + B_4 s^4 \tag{9}$$

where $t_\theta$ is the normalized integrated deflected angle and s is the normalized radial distance, now normalized to the radius of the core 11.

Figure 6:
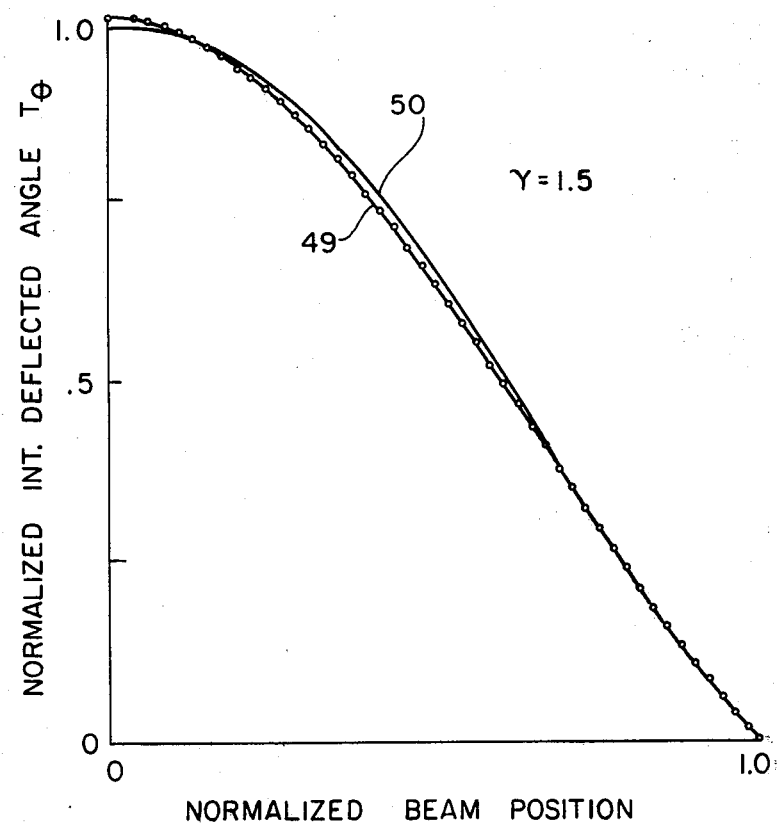
FIG. 6 is a polynomial curve fitted to theoretical integrated deflected angle data.

FIG. 6 shows the curve of the resulting polynomial 50 and the original theoretical date for $\gamma = 1.5$; the polynomial fit does deviate a small amount from the data. This deviation becomes minimal when the polynomial curve 50 is fitted to the curve for $\gamma = 2.0$. By determining polynomial equations for a number of theoretical curves having different $\Delta$'s and $\gamma$'s, the coefficients $B_2$ and $B_4$ can be plotted as a function of those parameters as shown in FIGS. 7 and 8.

Figure 7:
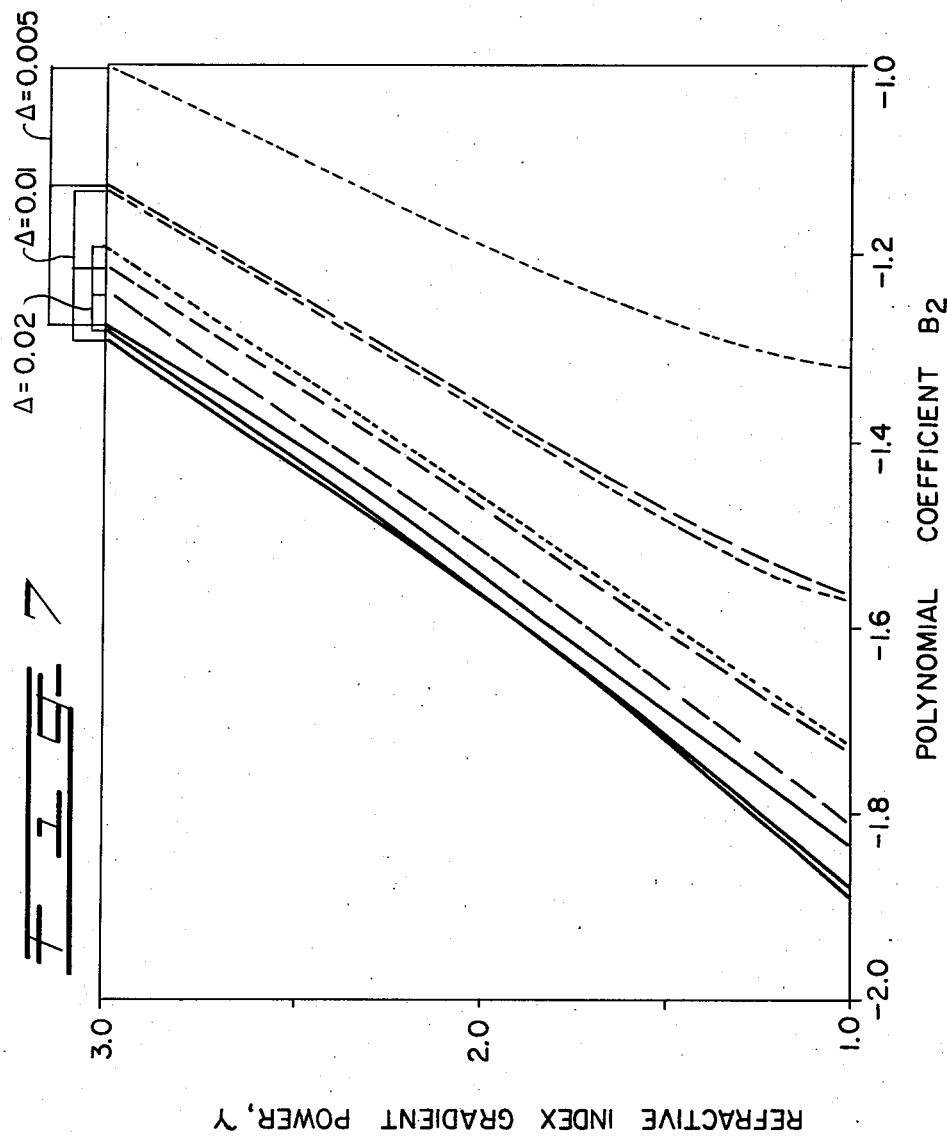
FIG. 7 is a curve representing the theoretical relation between the refractive index gradient power $\gamma$ and coefficient $B_2$.
Figure 8:
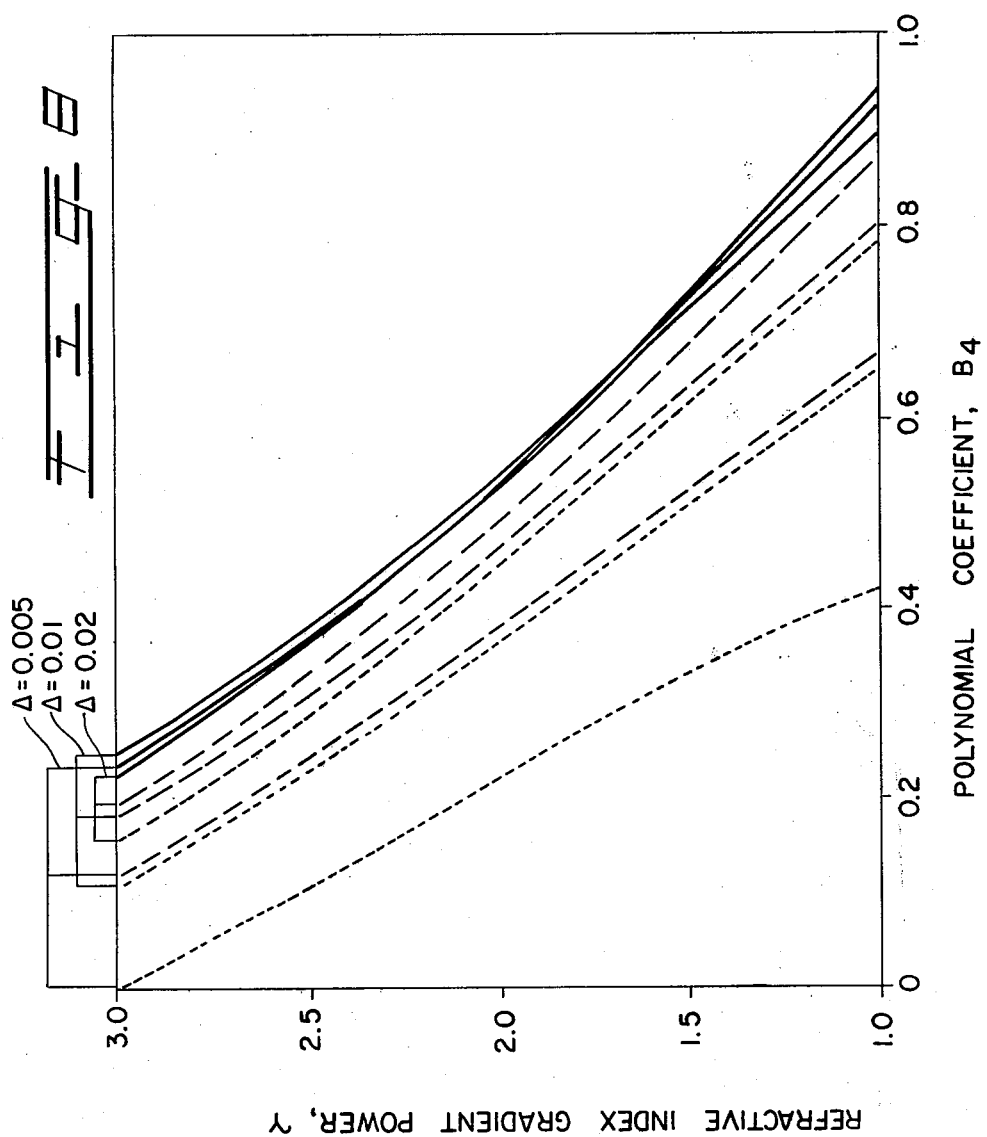
FIG. 8 is a curve representing the theoretical relation between the refractive index gradient power $\gamma$ and coefficient $B_4$.

A fourth order polynomial equation is also fitted to the experimental curve 47 and the coefficients $B_2$ and $B_4$ used to determine the refractive index gradient power $\gamma$ using FIGS. 7 and 8. It should also be obvious that the data that the curves in FIGS. 7 and 8 represent can be stored in a computer memory as a "look-up" table for ready access to the desired information.

Initially, the value of the refraction index ratio, $\Delta$, required in conjunction with the polynomial coefficients $B_2$ and $B_4$ to determine $\gamma$ is the nominal target value used during the fabrication process. Once $\gamma$ has been determined, $\Delta$ may accurately be calculated as will be hereinafter discussed. The steps may then be repeated with the new value of $\Delta$ to improve the accuracy.

It should also be noted that a value of $\gamma$ will be obtained for each of the coefficients $B_2$ and $B_4$ in FIGS. 7 and 8, respectively. Theoretically, the results should be identical; however, there may be small differences due to inaccuracies associated with the curve fitting techniques used. Therefore, an average of the two values of $\gamma$ are used to obtain the final value.

Figure 9:
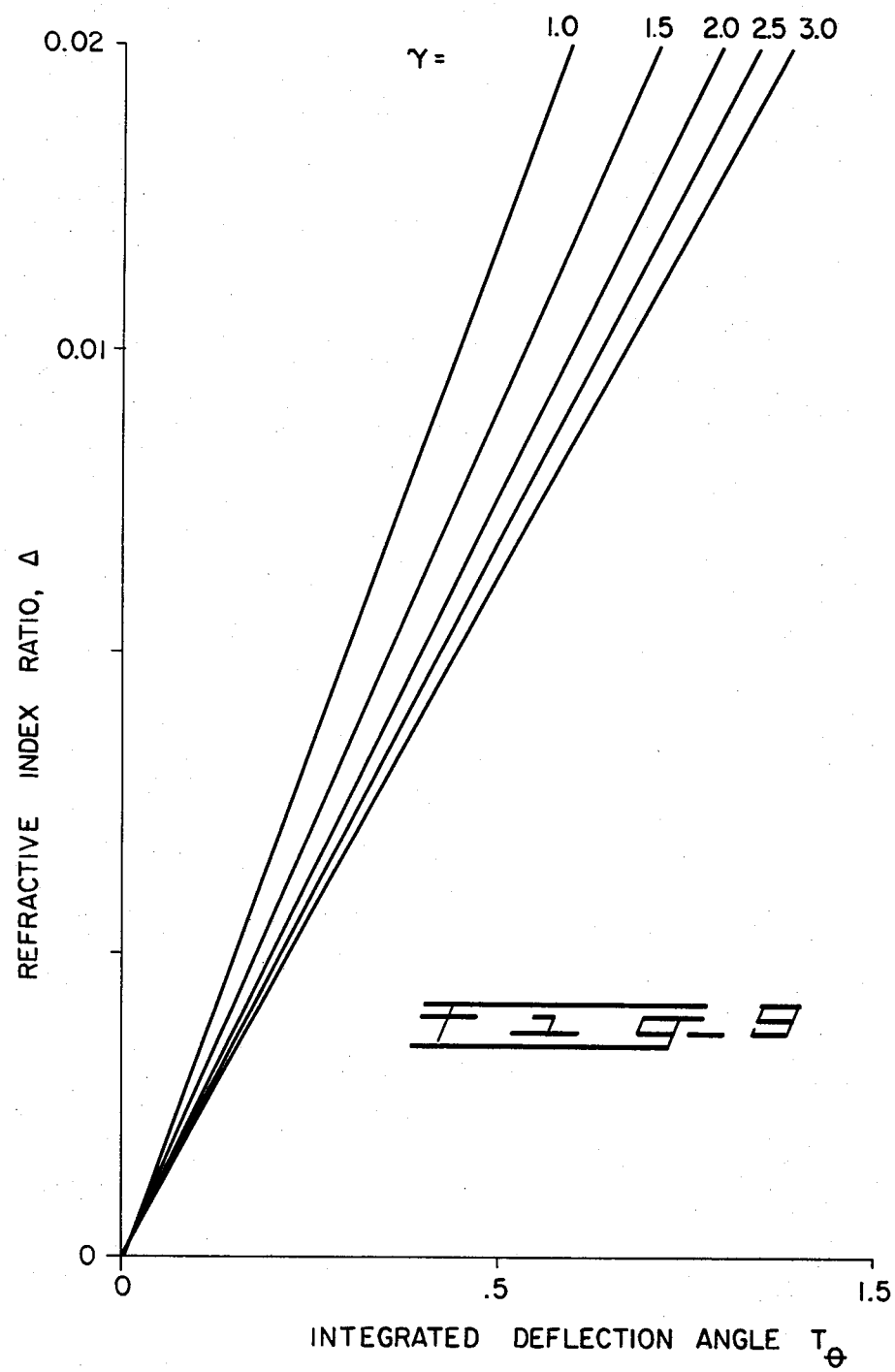
FIG. 9 depicts the variation of the integrated deflected angle peaks with the refractive index ratio, $\Delta$.
Figure 10:
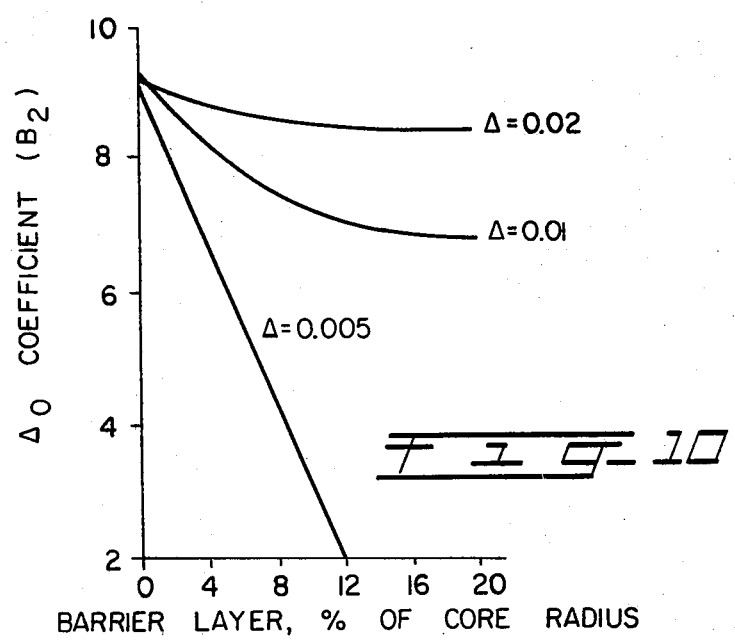
FIGS. 10 to 15 are plots of coefficients $A_i$ for coefficients $B_2$ and $B_4$.
Figure 11:
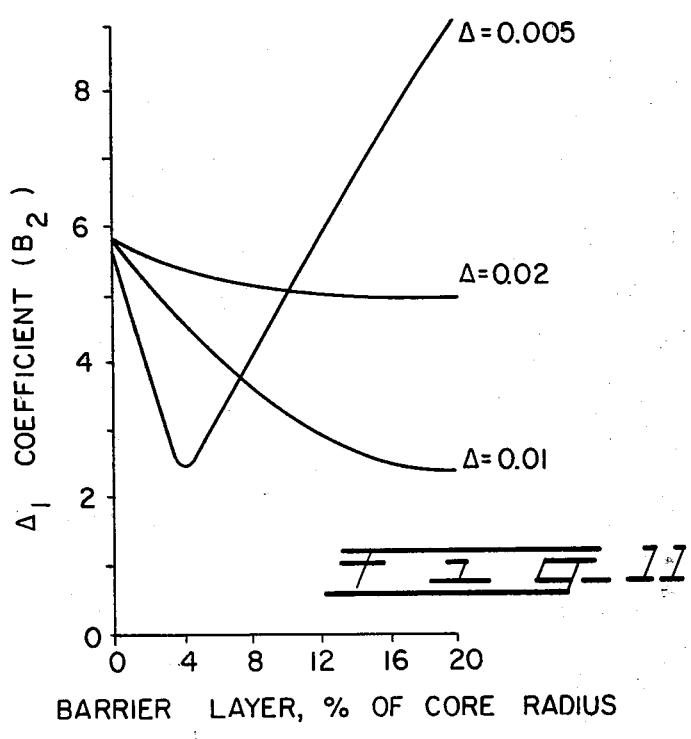
Figure 12:
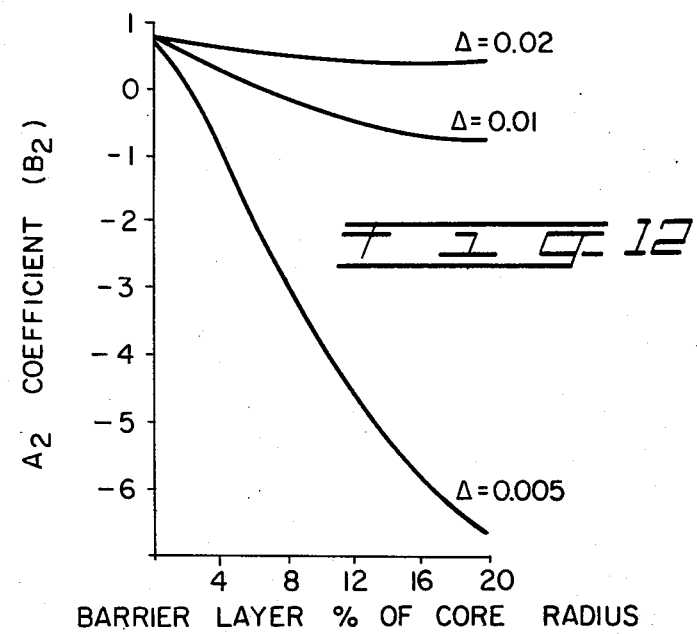
Figure 13:
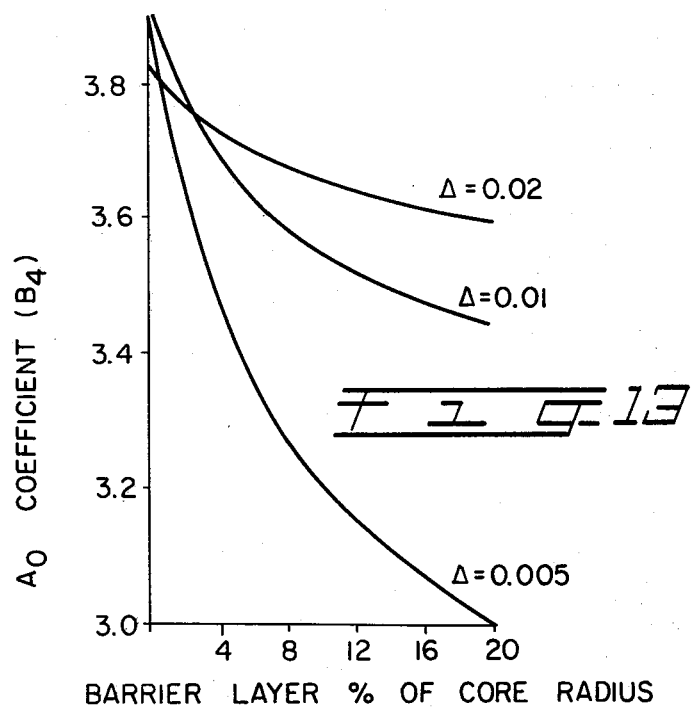
Figure 14:
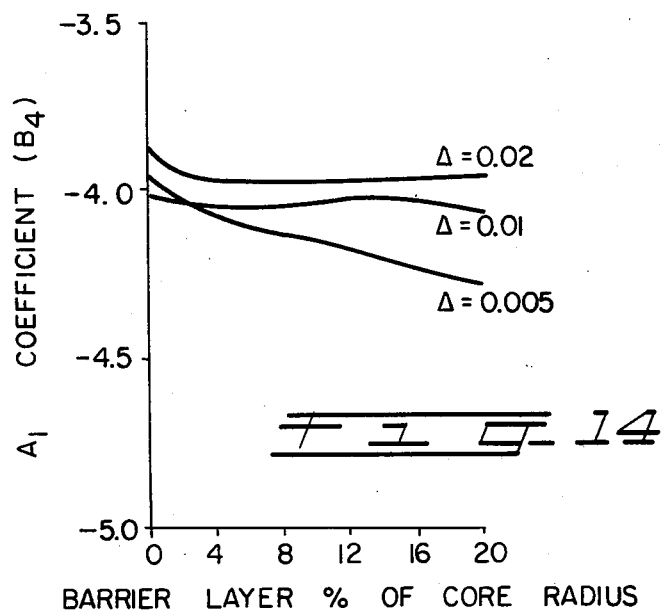
Figure 15:
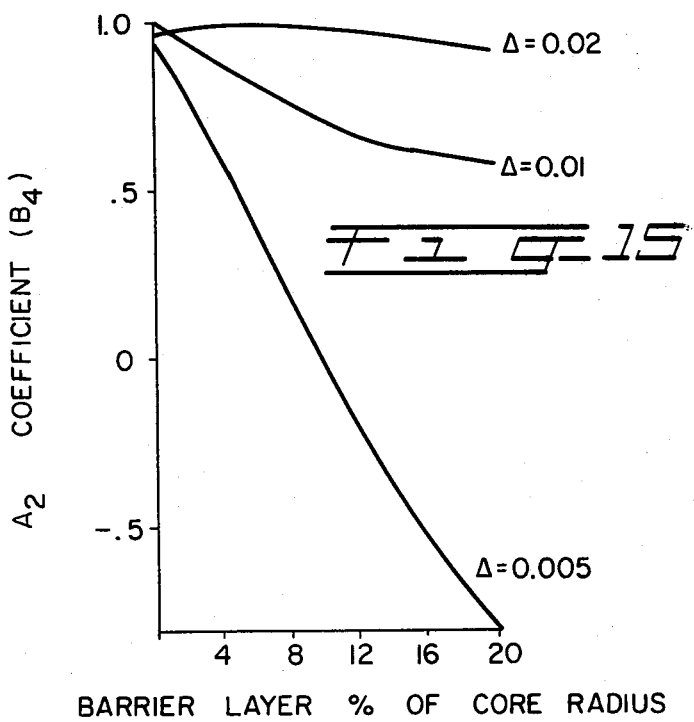

An accurate value of the refractive index ratio $\Delta$ can now be determined by comparing the peak $T_p$ of the experimental integrated angle curve 47 with the theoretical curve 49. FIG. 9 is a plot of the variation of the integrated deflection angle peak, $T_p$, for various values of refractive index gradient power $\gamma$. The curves are linear for specific values of $\gamma$ and an empirical formula for calculating $\Delta$ is, $$\Delta = T_p / K \gamma^{0.41} \tag{10}$$

where K is calibration constant.

As can be seen in the curves of FIG. 9, for a particular value of refractive index gradient power $\gamma$, the peak of the integrated angle $T_p$, is linearly proportional to the refractive index ratio $\Delta$.

The presence of a barrier layer does modify the relationship between the coefficients and the refractive index gradient power $\gamma$. Thus, for a more accurate determination of $\gamma$, the characteristics of the barrier layer must be factored in, as well as the refractive index ratio $\Delta$.

The plots of $B_2$ and $B_4$ against index power gradient $\gamma$ in FIGS. 7 and 8 are not perfectly linear and so this relationship was also described by a polynomial;

$$\gamma = A_o + A_1(B_i) + A_2(B_i)^2 \tag{11}$$

The coefficients, $A_i$, depend on the barrier layer characteristics and the refractive index ratio, $\Delta$. The coefficients $A_i$ for $B_2$ and $B_4$ are plotted in FIGS. 10 to 15 as a function of barrier layer thickness for a series of refractive index ratios to permit selection of the appropriate values. In all these cases the barrier layer refractive index was taken as 1.4536 (wavelength, $\lambda = 0.6328 \, \mu m$).

Table I shows the results of the instant technique compared to interferometry measurements. The preforms 10 tested were typical 8 mm diameter Germanium doped preforms. Since the parameters of the preforms 10—10 were measured after the optical fiber was drawn, the two measurements do not correspond to the same point along the preform and so the accuracy of the comparison is limited. However, the results show that the worst disagreement is 11% in the refractive index gradient power $\gamma$ and 8.6% for the refractive index ratio $\Delta$. It is expected that further refinement of the instant technique and the curve fitting procedure will reduce these discrepancies.

TABLE I

| PREFORM # | PARAMETER | PREFORM MEASUREMENT USING DEFLECTION ANGLE TECHNIQUE | FIBER MEASUREMENT USING SLAB INTERFEROMETRY (THREE SEPARATE MEASUREMENTS) | | |
|---|---|---|---|---|---|
| A | $\Delta$ | 0.0114 | 0.0124 | 0.0121 | 0.0125 |
|   | $\gamma$ | 1.706 | 1.64 | 1.865 | 1.85 |
| B | $\Delta$ | 0.0118 | 0.0110 | 0.0112 | — |
|   | $\gamma$ | 1.672 | 1.63 | 1.73 | — |
| C | $\Delta$ | 0.0118 | 0.0124 | 0.0117 | 0.0101 |
|   | $\gamma$ | 1.794 | 1.88 | 2.02 | 1.95 |

What is claimed is:

1. A method of determining parameters of a cylindrical optical fiber preform having a core and a cladding, comprising the steps of:
    scanning at least a portion of the cylindrical surface of the preform with a narrow, parallel scanning beam of coherent light, the parallel scanning beam being located within a plane which is perpendicular to the longitudinal axis of the preform, said beam passing through and being refracted by said preform;
    detecting the angular deflections of the refracted scanning beam exiting the preform; and
    comparing the detected angular deflections of the scanning beam with angular deflections of beams passing through preforms having known parameters to determine the parameters of the preform.

2. The method as set forth in claim 1, wherein:
    the detected angular deflections are compared with empirically developed detected angular deflections of the parallel scanning beam passing through preforms having known parameters.

3. The method as set forth in claim 1, wherein:
    the detected angular deflections are compared with theoretically determined angular deflections of the parallel scanning beam in preforms having known parameters.

4. The method as set forth in claims 2 or 3 wherein:
    the parameters to be determined are the refractive index gradient power $\gamma$ and the refractive index ratio $\Delta$.

5. The method as set forth in claim 1, characterized by:
    immersing the preform in oil prior to the scanning step.

6. A method of determining the acceptability of the uniformity and homogeneity of deposited layers in a cylindrical optical fiber preform having a cladding about a graded index core, comprising the steps of:
    scanning at least a portion of the cylindrical surface of the preform with a narrow, parallel scanning beam of coherent light, the parallel scanning beam being located within a plane which is perpendicular to the longitudinal axis of the preform, said beam passing through and being refracted by said preform;
    detecting the angular deflection of the beam as the beam exits the preform; and
    comparing the detected angular deflections of the beam with angular deflections of the beam through preforms having acceptable ranges of uniformity and homogeneity.

7. The method as set forth in claim 6, characterized by:
    immersing the preform in oil prior to the scanning step.

8. A method of non-destructively determining the refractive index gradient power, $\gamma$, in a cylindrical optical fiber preform having a cladding about a graded index core, comprising the steps of:
    (1) scanning at least a portion of the surface of the preform with a narrow, parallel scanning beam of coherent light, the parallel scanning beam being located within a plane which is perpendicular to the longitudinal axis of the preform, said beam passing through and being refracted by said preform;
    (2) detecting the angular deflection of the light beam as the beam exits the preform;
    (3) plotting a curve of the detected deflection angle versus the position of the scanning light beam;
    (4) integrating the curve of the detected deflected angle;
    (5) fitting a polynomial curve to the integrated deflection angle curve; and
    (6) determining the refractive index gradient power, $\gamma$, by comparing the coefficients of the polynomial to theoretically developed curves of the polynomial coefficients versus $\gamma$.

9. The method as set forth in claim 8, wherein the refractive index ratio, $\Delta$, is determined in accordance with the following equation:

$$\Delta = T_p/K\gamma^{0.41}$$

$T_p$ is the peak value of the integrated deflection angle curve,
K is a calibration constant,
$\gamma$ is the refractive index gradient power.

10. Apparatus for determining parameters of a cylindrical optical fiber preform having a core and a cladding, comprising:

means for scanning at least a portion of the cylindrical surface of the preform with a narrow, parallel scanning beam of coherent light, the parallel scanning beam being located within a plane which is perpendicular to the longitudinal axis of the preform, said beam passing through and being refracted by said preform;

means for detecting the angular deflection of the beam as the beam exits the preform; and means for comparing the detected angular deflections of the beam with angular deflections passing through preforms having known parameters to determine the parameters of the preform.

11. The apparatus as set forth in claim 10, wherein: the optical fiber preform is immersed in oil.

12. The apparatus as set forth in claim 10, wherein: the parameters to be determined are the refractive index gradient power $\gamma$ and the refractive index ratio $\Delta$.

* * * * *